United States Patent [19]

Himmler et al.

[11] Patent Number: 5,423,217

[45] Date of Patent: Jun. 13, 1995

[54] MEASURING APPARATUS FOR MEASURING FORCES WHICH OCCUR WHEN A ROTARY BODY IS CLAMPED ON A TESTING MACHINE DRIVE SHAFT

[75] Inventors: Günther Himmler, Darmstadt; Werner Bickelhaupt, Modautal, both of Germany

[73] Assignee: Hofmann Maschinenbau GmbH, Pfungstadt, Germany

[21] Appl. No.: 95,511

[22] Filed: Jul. 26, 1993

[30] Foreign Application Priority Data

Sep. 4, 1992 [DE] Germany ............... 42 29 593.9

[51] Int. Cl.⁶ ........................................... G01M 1/00
[52] U.S. Cl. ........................................... 73/487; 73/485
[58] Field of Search ............... 73/66, 485, 487, 146, 73/460–462, 862.542, 862.632, 862.635, 862.642, 862.045, 862.05, 862.06, 862.338

[56] References Cited

U.S. PATENT DOCUMENTS

| | | | |
|---|---|---|---|
| 2,697,853 | 12/1954 | Smyser | 73/485 |
| 3,352,732 | 11/1967 | Darr | 73/485 |
| 3,517,558 | 6/1970 | Kushmuk et al. | 73/485 |
| 4,748,844 | 6/1988 | Yoshikawa et al. | 73/146 |

FOREIGN PATENT DOCUMENTS 159049  11/1963  U.S.S.R. ............... 73/816.542

*Primary Examiner*—Robert Raevis
*Attorney, Agent, or Firm*—Cushman, Darby & Cushman

[57] ABSTRACT

A measuring apparatus for measuring forces which occur when a rotary body is clamped on a testing machine drive shaft include a face clamping force measuring means for measuring face clamping forces acting between said rotary body and a clamping element contact face which is disposed perpendicularly to the axis of the rotary body, and/or a radial clamping force measuring means for measuring a radial clamping force acting between said rotary body and a radially outwardly acting clamping means.

15 Claims, 3 Drawing Sheets

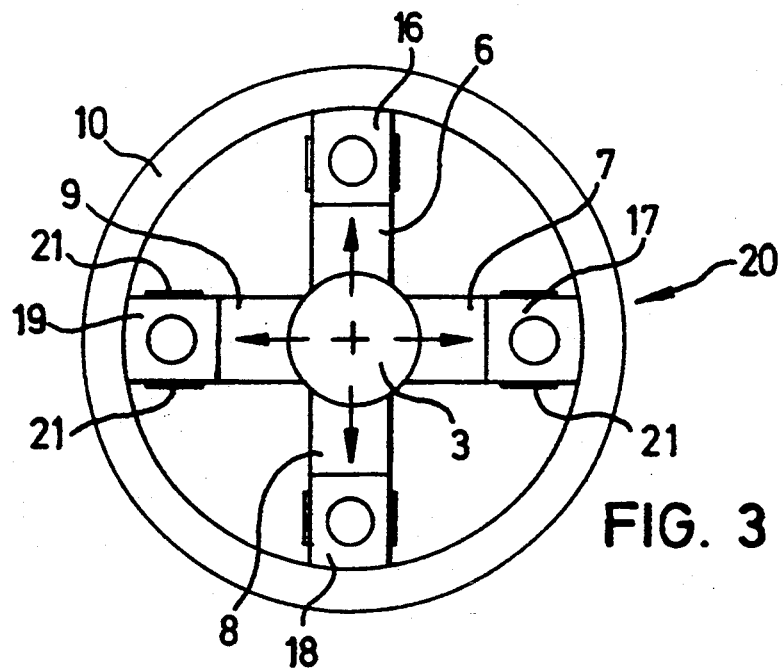
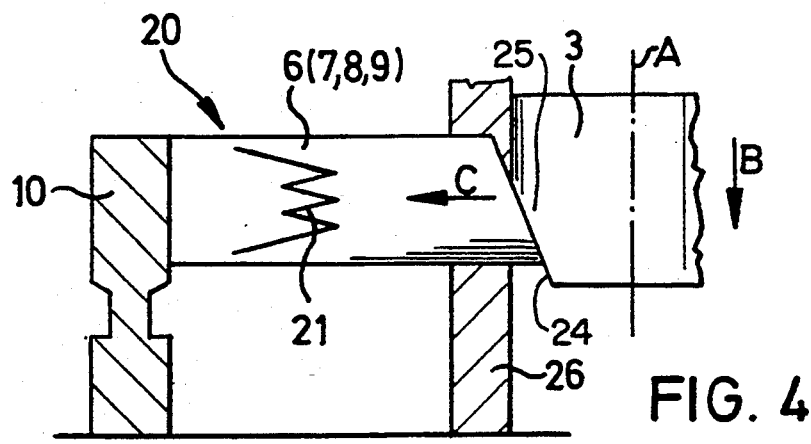
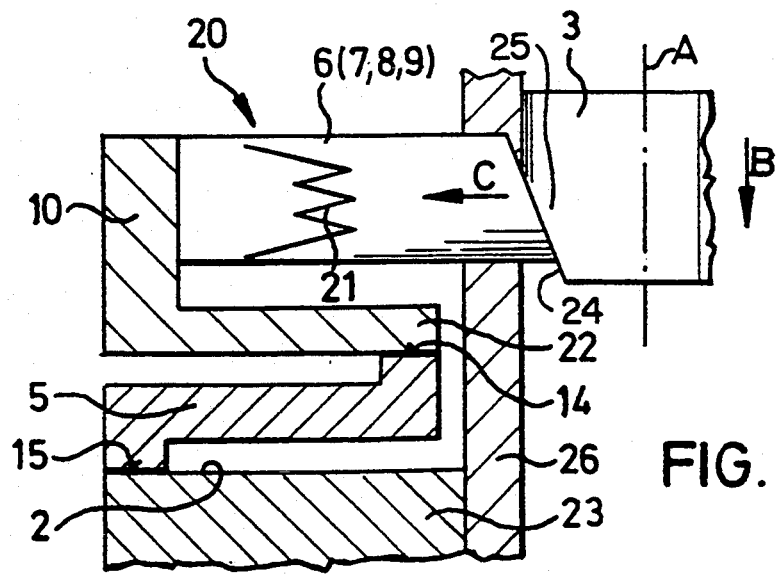

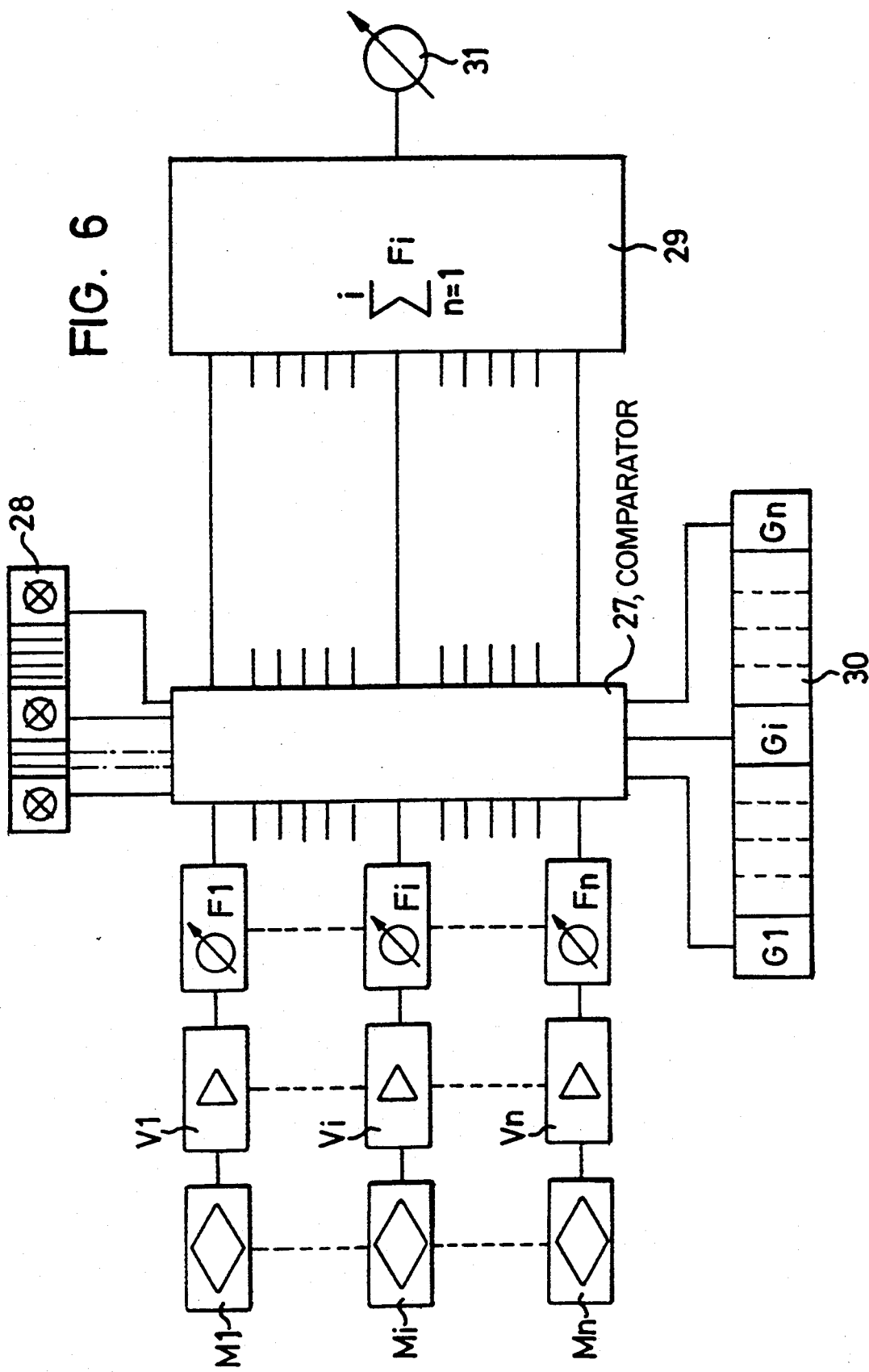

MEASURING APPARATUS FOR MEASURING FORCES WHICH OCCUR WHEN A ROTARY BODY IS CLAMPED ON A TESTING MACHINE DRIVE SHAFT

BACKGROUND OF THE INVENTION

The invention relates to a measuring apparatus for measuring forces which occur when clamping a rotary body on to a drive shaft of a testing machine, for example a balancing machine.

In this specification the term rotary body is used to denote a rotary member such as a wheel which may be in need of balancing, and a rotary member substitute body which is adapted for example to simulate a characteristic of a rotary member, such as for example its rigidity or strength as in a radial direction.

The purpose of conventional clamping arrangements as are used for example as an ancillary device on a wheel balancing machine for holding a wheel to be balanced in position for the balancing operation is to provide for radial centering of the workpiece or rotary member to be balanced, and to provide for reliable transmission of the drive moment from the drive shaft to the workpiece or rotary member which is carried on the drive shaft itself, without slippage of the rotary member. In that situation however the workpiece or rotary member is to be clamped in position in such a way that no surface pressure phenomena or markings or the like remain on the member.

SUMMARY OF THE INVENTION

An object of the present invention is to provide a measuring apparatus for measuring forces which occur when a rotary body is clamped on a testing machine drive shaft, which makes it possible to detect the forces which are required for transmission of a drive moment to the rotary member, in such a way as to protect and deal with it gently, in order to produce correct measurement values when testing the rotary member.

Another object of the present invention is to provide a measuring apparatus for measuring a force which occurs when clamping a rotary body on a drive shaft of a balancing machine, which provides for accurate measurement of the force involved using a simple structure and affording simplicity of operation.

In accordance with the principles of the present invention the foregoing and other objects are achieved by a measuring apparatus for measuring forces which occur when a rotary body is clamped on a drive shaft of a testing machine such as a balancing machine. The apparatus has a face clamping force measuring means for measuring a face clamping force which is operative between the rotary body, which can be a rotary member to be balanced or a rotary member substitute body, as indicated above, and a clamping element contact face which extends perpendicularly to the axis of rotation of the rotary body, and/or a radial clamping force measuring means for measuring a radial clamping force operative between a radially outwardly acting clamping means and the rotary body.

As will be seen in greater detail hereinafter with reference to preferred embodiments, by virtue of detecting radially acting clamping forces, it is possible to effect monitoring of the forces which are required for reliable transmission of the drive moments and in particular start-up moments which are to be transmitted from the drive shaft to the workpiece or rotary member, which forces are to be are of such a magnitude that they do not damage the workpiece or rotary member, more especially due to residual surface pressure phenomena such as markings thereon. For correct measurement of the dynamic unbalance of the rotary member which is clamped in position on the testing machine drive shaft, it is essential to measure and possibly suitably correct corresponding face clamping forces which act between the rotary member to be balanced and the support flange which extends perpendicularly to the axis of rotation of the rotary member for supporting the rotary member. By comparison with prescribed forces, that achieves an enhanced degree of measuring accuracy and reliability in the rotary member testing and measuring operations.

The face clamping force measuring means and/or the radial clamping force measuring means may be in the form of measuring devices which are integrated into the clamping assembly for clamping the rotary member on to the drive shaft. However, each such means may also be in the form of a separate measuring assembly. If the measuring means are integrated into the clamping arrangement, continuous monitoring of the face clamping and/or radial clamping forces can also be effected during the testing operation and/or during the measuring operation to be carried out on the rotary member. Any departure in regard to those forces from appropriate reference values or limit values can then be signalled in good time. Particularly in an adjustment operation, the measured forces can be used for achieving the desired positioning of the rotary member to be measured, on the shaft of the testing machine.

Further objects, features and advantages of the present invention will be apparent from the following description of preferred embodiments.

BRIEF DESCRIPTION OF THE DRAWING

FIG. 3 is a front view of an embodiment of a radial clamping force measuring means, FIG. 4 is a partly sectional view of part of the radial clamping force measuring means shown in FIG. 3, FIG. 5 is a view corresponding to that shown in FIGS. 1 and 4 of a further embodiment of a combined measuring arrangement for measuring both radial and face clamping forces, and FIG. 6 shows a block circuit diagram of an evaluation arrangement for the measurement signals.

DESCRIPTION OF PREFERRED EMBODIMENTS

Figure 1:
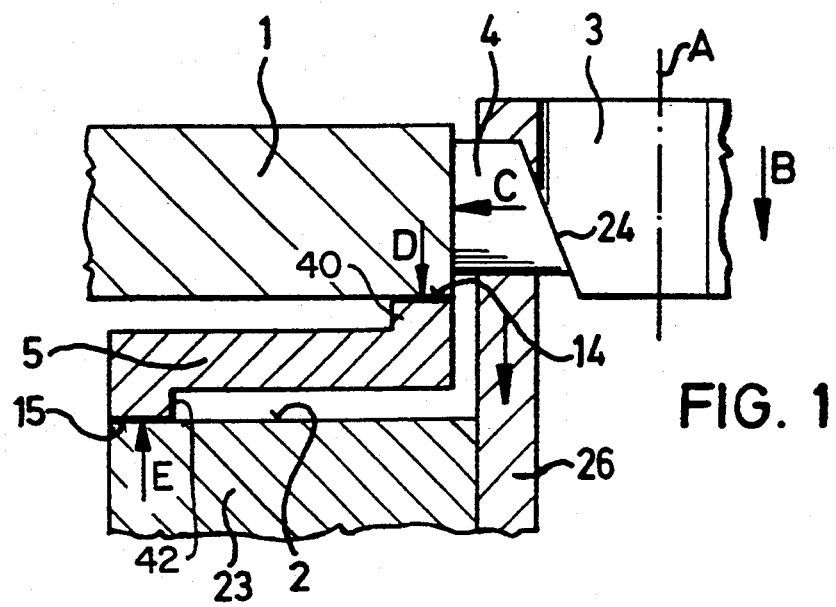
FIG. 1 is a partly sectional view of part of a first embodiment of a construction in accordance with the invention.

Referring firstly to FIG. 1, reference numeral 1 therein denotes a workpiece such as a rotary member, for example a wheel, which can be clamped by means of suitable clamping devices on a drive shaft (not shown) of a testing machine, for example a balancing machine. The rotary member 1 is then mounted rotatably about its axis A of rotation on the drive shaft of the testing machine. The clamping means used comprise a clamping mandrel or bar 3 which is arranged to be axially displaceable in the direction indicated by the arrow B in FIG. 1. The clamping bar 3 has a taper surface 24 with which it bears against a corresponding taper surface 25 on each of a plurality of radially movably mounted clamping jaws 4.

Upon axial displacement of the clamping bar 3 in the direction indicated by the arrow B, the clamping jaws 4 are thus displaced radially outwardly in the direction indicated by the arrow C. Both the clamping bar 3 and also the radially outwardly displaceable clamping jaws 4 can be suitably guided on a guide arrangement 26. The guide arrangement 26 is connected to the drive shaft of the machine in any suitable manner (the form of connection involved is not shown).

Figure 2:
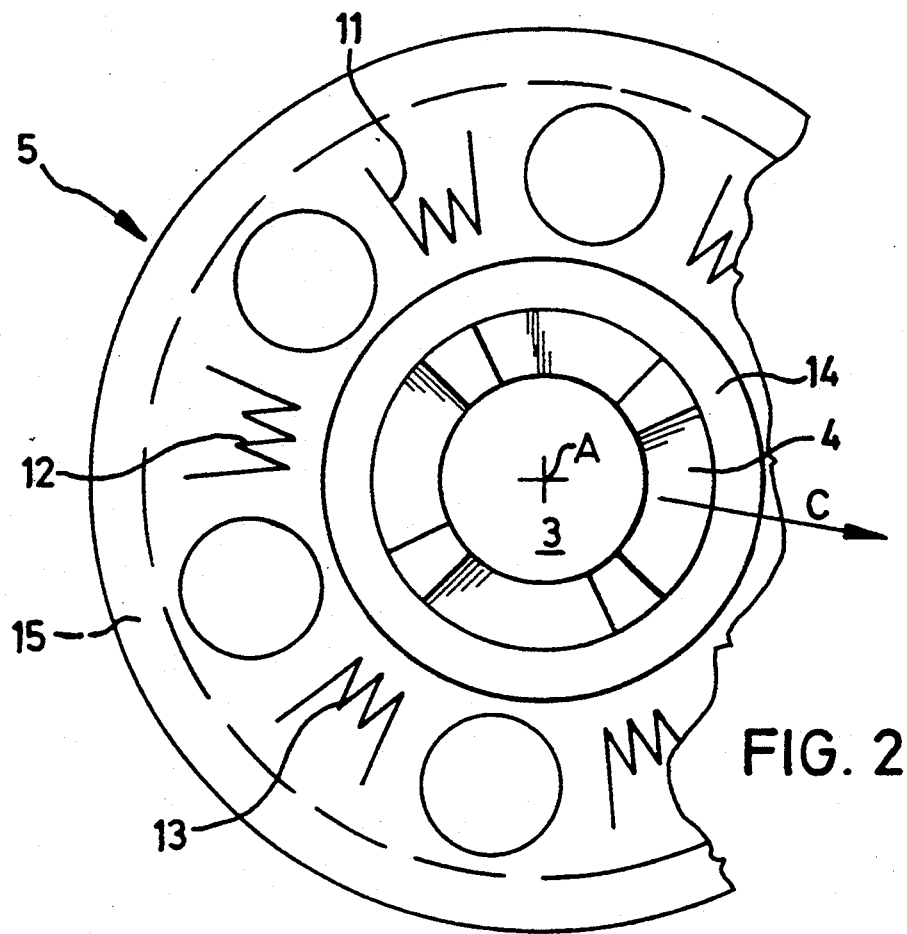
FIG. 2 shows a front view of a face clamping force measuring means which is used in the FIG. 1 structure.

It will be seen from FIG. 1 that the illustrated structure involves face clamping forces which are operative as indicated by the arrows D and E between the rotary member 1 to be clamped on the drive shaft and a clamping element contact face 2 which is provided on a mounting ring or flange of which part is shown at 23. The FIG. 1 structure has a face clamping force measuring means which serves to detect those face clamping forces, as is shown in FIG. 2 to which reference will now be made.

The face clamping force measuring means is in the form of an annular measuring body or measuring ring generally indicated by reference numeral 5. Force measuring devices 11, 12 and 13 which may comprise wire strain gauges are arranged around the axis of rotation A at at least substantially equal angular spacings. The measuring ring 5 has a contact face as indicated at 14 in FIGS. 1 and 2, which is formed on a projection portion of the measuring ring 5 and by which the measuring ring 5 bears against an adjacent surface of the rotary member 1 and transmits forces indicated by arrow D. The measuring ring 5 also has a contact face indicated at 15 in FIGS. 1 and 2, which is formed on a projection portion 42 of the measuring ring and with which the measuring ring bears against the clamping element contact face 2 of the mounting ring 23 for transmitting forces indicated by arrow E. The projection 40 having the contact face 14 is disposed in the region of the inside periphery of the measuring ring 5 on one side thereof while the projection portion 42 with the contact face 15 is disposed in the region of the outside periphery on the other side of the measuring ring. In the embodiment illustrated in FIGS. 1 and 2 the mounting ring 23 forms part of the clamping arrangement and can be connected to the guide arrangement 26 in any suitable fashion (not shown). The contact face 2 and the contact faces 14 and 15 provided on the projection portions on the measuring ring 5 extend perpendicularly to the axis A of the rotary member 1.

Looking now at FIGS. 3 and 4, in the embodiment of a radial clamping force measuring means shown therein, a rotary member substitute body 10 is illustrated in the form of a counterpart holding ring. The body 10 simulates a given level of radial rigidity or radial strength of the rotary member 1. The radial clamping force measuring means which is generally indicated by reference 20 in FIGS. 3 and 4 has radially displaceable clamping jaws 6, 7, 8 and 9 which are suitably guided on the guide arrangement 26. The clamping jaws which are radially movable in the direction indicated by the arrow C in FIG. 4 are provided with suitable force measuring elements 16, 17, 18 and 19 which may have strain gauges 21. The force to produce a radial force which is directed outwardly in the direction indicated by the arrow C in FIG. 4 can be produced by means of the clamping bar 3 which, as in the embodiment shown in FIG. 1, bears by way of taper surfaces against the radially movable clamping jaws 6 through 9. The radial clamping forces which come into operation when the clamping bar 3 is displaced can be detected by means of the force measuring elements 16 through 19.

In the embodiment shown in FIG. 5, the measuring assembly comprises both the face clamping force measuring means 5 described with reference to FIGS. 1 and 2 and also the radial clamping force measuring means 20 described with reference to FIGS. 3 and 4. In this case the substitute body 10 also has an annular contact limb 22 which provides a contact face for the contact face 14 on the inward projection portion of the measuring ring 5. In other respects the radial clamping force measuring means 20 and the face clamping force measuring means 5 are of the same design configurations as was described above with reference to FIGS. 1 through 4.

It is also possible for the clamping jaws 4 in FIG. 1 to be provided with force measuring elements as shown in the embodiments of FIGS. 3 through 5. That then provides for continuous measurement of the radial and face clamping forces during a rotary member testing or measuring operation.

FIG. 6 shows a block circuit diagram of a signal evaluation arrangement for the force measurement signals. Those signals at the individual measurement locations, which are parts of measurement bridges M1 ... Mi ... Mn are passed by way of bridge amplifiers V1 ... Vi ... Vn to clamping force display devices F1 ... Fi ... Fn. Preset limit values G1 ... Gi ... Gn for the clamping forces are stored in a limit value storage arrangement 30. The measured clamping forces F1 ... Fi ... Fn are compared to the limit values G1 ... Gi ... Gn in a comparator 27. Any departure of the measured forces from the limit values is signalled by means of a signal display device 28. The measured clamping forces are also passed to a summing means 29 where all measured clamping forces are summed to give a sum clamping force which is then displayed in a display device 31.

It will be appreciated that the above-described constructions have been set forth solely by way of example and illustration of the principles of the present invention and that various modifications and alterations may be made therein without thereby departing from the spirit and scope of the present invention.

What is claimed is:

1. A measuring apparatus for measuring clamping force developed between a rotary body and a drive mechanism of a test machine to which the rotary body is clamped comprising means for clamping a rotary body to a drive mechanism, to permit the rotary body to be rotated about an axis, by generating force between the rotary body and the drive mechanism and means for measuring clamping force as such force is developed between said rotary body and said drive mechanism during clamping,
   wherein said clamping force measuring means comprises a deformable annular member and force measuring members carried by the annular member and distributed around the rotation axis of said rotary body at substantially uniform angular spacings.

2. Apparatus as in claim 1 wherein said clamping means includes a clamping element face.

3. Apparatus as in claim 2 wherein said clamping element face extends perpendicularly to the rotation axis of said rotary body.

4. Apparatus as in claim 1 wherein said annular member includes inside periphery and outside periphery edge regions and a flat annular face located at each of said inside and outside periphery edge regions.

5. Apparatus as in claim 4 wherein each said flat annular face extends at least substantially perpendicularly to the rotation axis of said rotary body.

6. Apparatus as in claim 4 wherein said flat annular face located at the inside periphery edge region is adapted to contact said rotary body.

7. Apparatus as in claim 4 wherein said flat annular face located at the outside periphery edge region is adapted to contact a clamping element face of said clamping means.

8. Apparatus as in claim 4 wherein said annular member includes an inside diameter and an outside diameter, and one of said flat annular faces is located in the region of an inside diameter of said annular member and on one side thereof and the other said flat annular face is located in the region of an outside diameter of said annular member and a side opposite said one side thereof.

9. Apparatus as in claim 8 wherein said flat annular face in the region of the inside diameter of said annular member is adapted to bear against said rotary body and the other flat annular face in the region of the outside diameter of the annular member is adapted to bear against a clamping element face of said clamping means.

10. Apparatus as in claim 1 wherein said rotary body clamping means comprises radially movable clamping jaw means and said measuring members are force measuring elements operatively associated therewith, said radially movable clamping jaw means being adapted to be movable against said rotary body.

11. Apparatus as in claim 10 wherein said body has an annular configuration.

12. Apparatus as in claim 1 wherein said force measuring members include force measuring strain gauge members.

13. Apparatus as in claim 1 wherein said clamping force measuring means is integrated into said clamping means.

14. Measuring apparatus for use with a testing machine for testing a rotary body comprising a drive mechanism and a clamping arrangement for clamping a rotary body to the drive mechanism including radially movable clamping jaws, and a measuring system comprised of force measuring elements provided on said radially movable clamping jaws for sensing and measuring clamping forces as such forces are developed during clamping.

15. Measuring apparatus for measuring forces developed when a body, to be rotated about an axis thereof, is clamped on a testing machine comprising a drive mechanism, a clamping system for securely clamping the body onto said drive mechanism, said clamping system including a clamp contact face extending perpendicularly to said axis of said body, and clamping force measuring means for measuring clamping force acting axially in relation to said body between said body and said contact face.

* * * * *